United States Patent
Kunihiro et al.

(10) Patent No.: US 12,333,852 B2
(45) Date of Patent: Jun. 17, 2025

(54) FACE DETECTION DEVICE

(71) Applicant: Mitsubishi Electric Corporation, Tokyo (JP)

(72) Inventors: Kazuki Kunihiro, Tokyo (JP); Taro Kumagai, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 402 days.

(21) Appl. No.: 17/793,744

(22) PCT Filed: Mar. 24, 2020

(86) PCT No.: PCT/JP2020/012916
§ 371 (c)(1),
(2) Date: Jul. 19, 2022

(87) PCT Pub. No.: WO2021/192007
PCT Pub. Date: Sep. 30, 2021

(65) Prior Publication Data
US 2023/0060049 A1 Feb. 23, 2023

(51) Int. Cl.
*G06V 40/16* (2022.01)
*G06V 20/59* (2022.01)

(52) U.S. Cl.
CPC ............ *G06V 40/161* (2022.01); *G06V 20/59* (2022.01); *G06V 40/168* (2022.01)

(58) Field of Classification Search
CPC .... G06V 40/161; G06V 20/59; G06V 40/168; A61B 5/18; G08G 1/16
See application file for complete search history.

(56) References Cited

FOREIGN PATENT DOCUMENTS

| JP | 2009-17194 A | | 1/2009 | |
| JP | 2010128961 A | * | 6/2010 | |
| JP | 2011-159214 A | | 8/2011 | |
| WO | WO-2018116373 A1 | * | 6/2018 | ............. B60N 2/002 |
| WO | WO 2019/030855 A1 | | 2/2019 | |

OTHER PUBLICATIONS

International Search Report (PCT/ISA/210) issued in PCT/JP2020/012916, dated Jun. 23, 2020.
Written Opinion of the International Searching Authority (PCT/ISA/237) issued in PCT/JP2020/012916, dated Jun. 23, 2020.
Japanese Office Action for JP 2022-509809, dated Apr. 4, 2023 with English translation.

* cited by examiner

*Primary Examiner* — Molly Wilburn
(74) *Attorney, Agent, or Firm* — Birch, Stewart, Kolasch & Birch, LLP

(57) ABSTRACT

A face detection device includes processing circuitry configured to acquire, from an imaging device mounted on a vehicle and imaging an at least one occupant inside the vehicle, a captured image in which the at least one occupant is imaged; set a search area in which a face of the at least one occupant is searched in the acquired captured image; search the search area and detect the face of the at least one occupant; determine whether or not the detection of the face of the at least one occupant has succeeded; and expand the search area when determining that the detection of the face of the at least one occupant has failed.

11 Claims, 7 Drawing Sheets

FACE DETECTION DEVICE

TECHNICAL FIELD

The present disclosure relates to a face detection device that is mounted on a vehicle and detects an occupant of the vehicle.

BACKGROUND ART

As a face detection device that detects a face of an occupant using an image obtained by imaging the occupant inside a vehicle, it is disclosed that an area (hereinafter, referred to as a search area) for searching for the face of the occupant is set in the image and a position where the face of the occupant is successfully detected is recorded, and when the detection of the face of the occupant fails, the position where the face of the occupant is successfully detected is preferentially searched again (see, for example, Patent Literature 1).

CITATION LIST

Patent Literatures

Patent Literature 1: JP 2010-128961 A

SUMMARY OF INVENTION

Technical Problem

However, in a case where the face to be detected moves out of the search area due to movement of the occupant or the like, there is a possibility that the face cannot be detected and the search area in which detection of the face of the occupant has failed is continuously searched.

The present disclosure has been made to solve the above-described problems, and an object of the present disclosure is to provide a face detection device capable of detecting a face of an occupant by expanding a search area even when the face of the occupant cannot be detected in the search area.

Solution to Problem

A face detection device according to the present disclosure includes: processing circuitry configured to acquire, from an imaging device mounted on a vehicle and imaging an at least one occupant inside the vehicle, a captured image in which the at least one occupant is imaged; set a search area in which a face of the at least one occupant is searched in the acquired captured image; search the search area and detect the face of the at least one occupant; and determine whether or not the detection of the face of the at least one occupant has succeeded, wherein the processing circuitry expands the search area when determining that the detection of the face of the at least one occupant has failed.

Advantageous Effects of Invention

According to the present disclosure, even when the detection of the face of the occupant fails, the detection accuracy is improved because the search area is expanded to detect the face of the occupant.

DESCRIPTION OF EMBODIMENTS

Hereinafter, embodiments will be described with reference to the drawings.

First Embodiment

Figure 1:
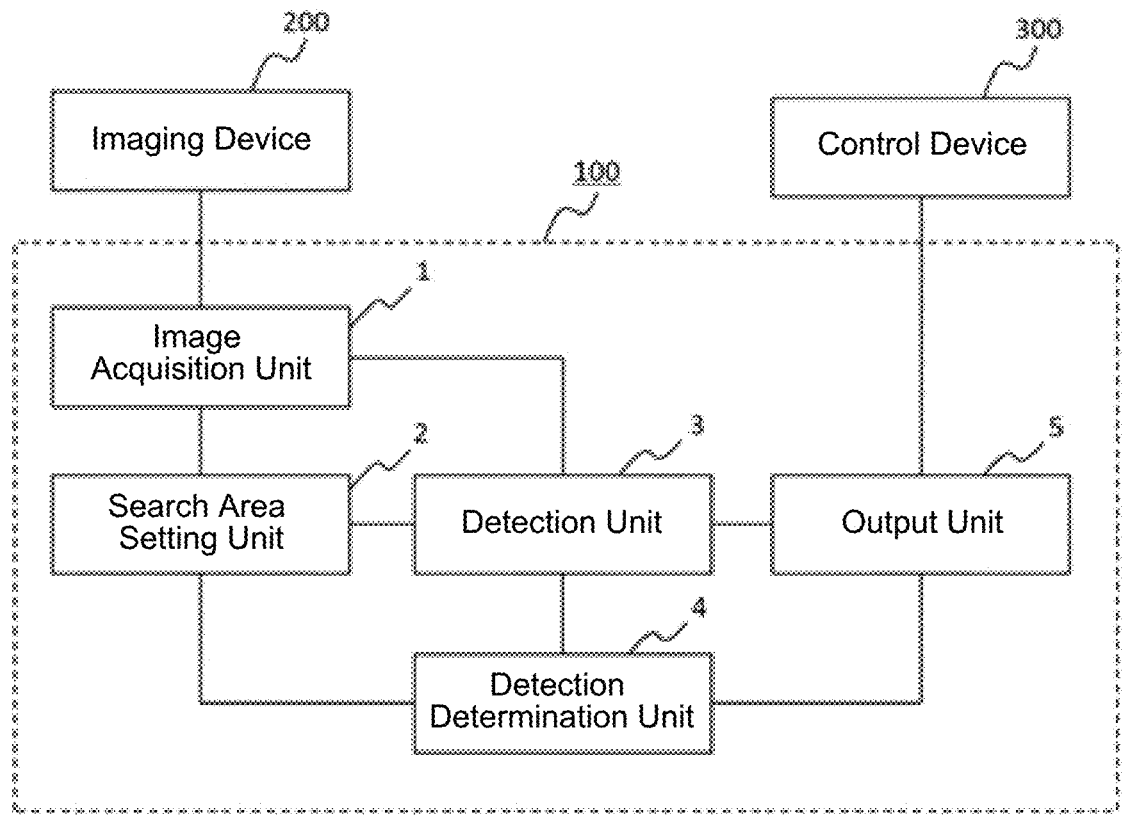
FIG. 1 is a block diagram schematically illustrating a configuration of a face detection device according to a first embodiment.

FIG. 1 is a block diagram schematically illustrating a configuration of a face detection device 100 according to a first embodiment. The face detection device 100 includes an image acquisition unit 1, a search area setting unit 2, a detection unit 3, and a detection determination unit 4. The face detection device 100 is connected to an imaging device 200 and a control device 300, and information related to detection of the face (hereinafter, referred to as face detection) of an occupant in an image captured by the imaging device 200 (hereinafter, referred to as a captured image) is output from an output unit 5 of the face detection device 100 to the control device 300. Here, at least one of the imaging device 200 and the control device 300 may be provided in the face detection device 100.

Figure 2:
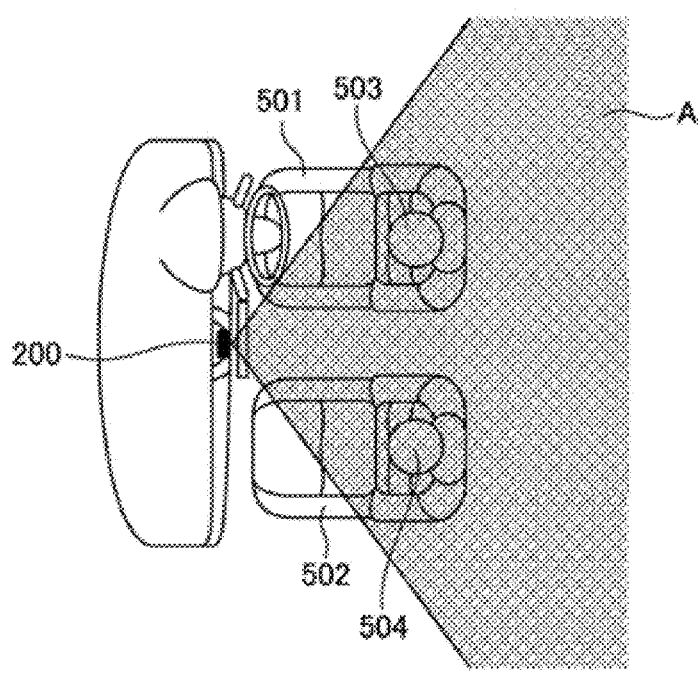
FIG. 2 is an explanatory diagram illustrating an imaging range of an imaging device according to the first embodiment.

FIG. 2 is an explanatory diagram illustrating an imaging range of the imaging device 200 according to the first embodiment. In FIG. 2, the inside of a vehicle on which the face detection device 100 is mounted is viewed from above. The imaging device 200 includes, for example, a wide-angle camera, an infrared camera, or the like. One or a plurality of imaging devices 200 is arranged on an instrument panel, a steering column, a rearview mirror, and the like so as to be able to simultaneously image at least occupants 503 and 504 seated on a driver's seat 501 and a passenger seat 502, respectively. Here, the imaging device 200 may include a back seat (not illustrated) in the imaging range. Hereinafter, the occupants 503 and 504 to be imaged by the imaging device 200 are also collectively referred to as "occupants". That is, the occupants include the driver.

The imaging device 200 images the inside of the vehicle at intervals of 30 to 60 frames per second (fps), for example, and outputs the captured image to the image acquisition unit 1 of the face detection device 100. In the example of FIG. 2, an imaging region of the imaging device 200 is indicated by an area A. In addition, it is preferable that the face detection device 100 perform face detection processing every time a captured image is acquired from the imaging device 200, that is, every frame.

The search area setting unit 2 sets a search area in which the detection unit 3 to be described below searches for the face of the occupant in the captured image acquired by the image acquisition unit 1. The search area is set, for example, on the basis of coordinates in the captured image. The setting of the search area will be described later.

The detection unit 3 analyzes the captured image and detects the face of the occupant in the search area. Then, the detection unit 3 acquires an area where the face of the occupant is detected (hereinafter, referred to as a face area) and feature information of the face of the occupant in the face area. When detecting the face of the occupant, the detection unit 3 acquires coordinates related to a face area surrounding the face of the occupant, such as a rectangle in contact with the contour of the face of the occupant, from the captured image. Here, for example, in a case where the face area is a rectangle, the coordinates related to the face area are coordinates of each vertex, the center, and the like of the rectangle. The detection unit 3 calculates the width, height, area, and the like of the face area from the coordinates of the face area. In addition, the feature information of the face of the occupant is, for example, a contrast ratio of elements of the face of the occupant, such as an eye, a nose, a mouth, and a cheek, after the size of the face is normalized. Then, the detection unit 3 outputs the acquired coordinates of the face area and feature information of the face of the occupant to the search area setting unit 2 and the detection determination unit 4. Here, the detection unit 3 preferably searches for the face of the occupant every time the image acquisition unit 1 acquires the captured image.

The detection determination unit 4 determines whether or not the detection unit 3 has succeeded in face detection using the feature information of the face of the occupant in the search area. For example, the detection determination unit 4 determines that the detection unit 3 has succeeded in face detection when determining that the luminance distribution of the face area is likely to be a face from the contrast ratio in the face area detected by the detection unit 3, and determines that the detection unit 3 has failed in face detection when determining that the luminance distribution is not likely to be a face.

The detection determination unit 4 may also determine that the face detection has failed when at least one of the width, the height, and the area of the face area detected by the detection unit 3 is equal to or smaller than a predetermined size or equal to or larger than a predetermined size. In this case, the detection determination unit 4 may acquire the coordinates of the face area from the detection unit 3 and determine whether or not the detection unit 3 has succeeded in face detection. Further, the detection determination unit 4 increments and records the number of times the detection unit 3 has determined that the face detection has failed. Here, the detection determination unit 4 may determine whether or not the luminance distribution in the face area detected by the detection unit 3 is likely to be a face by referring to training data stored in a recording unit (not illustrated).

The control device 300 is a device that controls the vehicle on which the face detection device 100 is mounted. Using the detection result of the face detection device 100, the control device 300 performs, for example, adjustment of the position and inclination of the seat of the driver's seat 501 and the passenger seat 502, control of a sound device, control of switching of a driving mode of the vehicle, and the like.

In addition, the control device 300 outputs a signal to cause the face detection device 100 to start the face detection operation, for example, in a case where any of the following is detected: a door is unlocked; a door is opened; a seat belt is worn; the ignition is turned on; a human detection sensor is turned on; a shift lever is moved to the drive position; the vehicle speed exceeds 0 km/h; the navigation device starts guiding; a host vehicle leaves home; and the like. On the other hand, for example, in a case where any of the following is detected: the seat belt is released; the ignition is turned off; the human detection sensor is turned off; the shift lever is moved to the parking position; the navigation device ends guiding; the host vehicle returns home; and the like, a signal indicating the end of the face detection operation is output to the face detection device 100.

Next, a hardware configuration example of the face detection device 100 will be described. FIG. 3 is a diagram illustrating a hardware configuration example of the face detection device according to the first embodiment. The image acquisition unit 1, the search area setting unit 2, the detection unit 3, the detection determination unit 4, and the output unit 5 of the face detection device 100 may be a processing circuit 100a that is dedicated hardware as illustrated in FIG. 3A, or may be a processor 100b that executes a program stored in a memory 100c as illustrated in FIG. 3B.

Figure 3A:
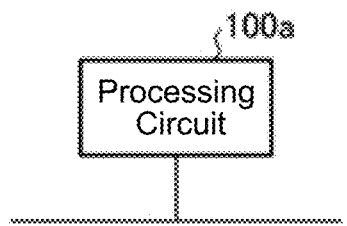
FIGS. 3A and 3B are diagrams illustrating a hardware configuration example of the face detection device according to the first embodiment.

As illustrated in FIG. 3A, in a case where the image acquisition unit 1, the search area setting unit 2, the detection unit 3, the detection determination unit 4, and the output unit 5 are dedicated hardware, the processing circuit 100a corresponds to, for example, a single circuit, a composite circuit, a programmed processor, a parallel-programmed processor, an application specific integrated circuit (ASIC), a field-programmable gate array (FPGA), or a combination thereof. Each of the functions of the image acquisition unit 1, the search area setting unit 2, the detection unit 3, the detection determination unit 4, and the output unit 5 may be implemented by a processing circuit, or the functions of the respective units may be collectively implemented by one processing circuit.

Figure 3B:
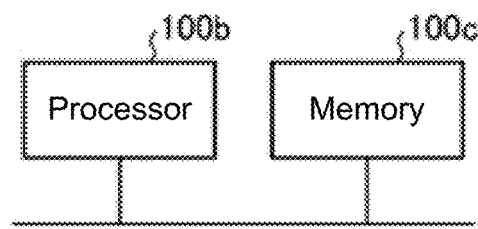

As illustrated in FIG. 3B, in a case where the image acquisition unit 1, the search area setting unit 2, the detection unit 3, the detection determination unit 4, and the output unit 5 are the processor 100b, the functions of the respective units are implemented by software, firmware, or a combination of software and firmware. The software or firmware is described as a program and stored in the memory 100c. The processor 100b reads and executes the program stored in the memory 100c to implement the functions of the image acquisition unit 1, the search area setting unit 2, the detection unit 3, the detection determination unit 4, and the output unit 5. That is, the image acquisition unit 1, the search area setting unit 2, the detection unit 3, the detection determination unit 4, and the output unit 5 include the memory 100c for storing a program that results in execution of each step illustrated in FIG. 5 to be described later when executed by the processor 100b. It can also be said that these programs cause a computer to execute procedures or methods performed by the image acquisition unit 1, the search area setting unit 2, the detection unit 3, the detection determination unit 4, and the output unit 5.

Here, the processor 100b is, for example, a central processing unit (CPU), a processing device, an arithmetic device, a processor, a microprocessor, a microcomputer, a digital signal processor (DSP), or the like. The memory 100c may be, for example, a nonvolatile or volatile semiconductor memory such as a random access memory (RAM), a read only memory (ROM), a flash memory, an erasable programmable ROM (EPROM), or an electrically EPROM (EEPROM), a magnetic disk such as a hard disk or a flexible disk, or an optical disk such as a mini disk, a compact disc (CD), or a digital versatile disc (DVD).

Note that some of the functions of the image acquisition unit 1, the search area setting unit 2, the detection unit 3, the detection determination unit 4, and the output unit 5 may be implemented by dedicated hardware, and some of them may be implemented by software or firmware. As described above, the processing circuit 100a in the face detection device 100 can implement the functions by hardware, software, firmware, or a combination thereof. In addition, at least some of the functions of the image acquisition unit 1, the search area setting unit 2, the detection unit 3, the detection determination unit 4, and the output unit 5 may be executed by an external server.

Figure 4:
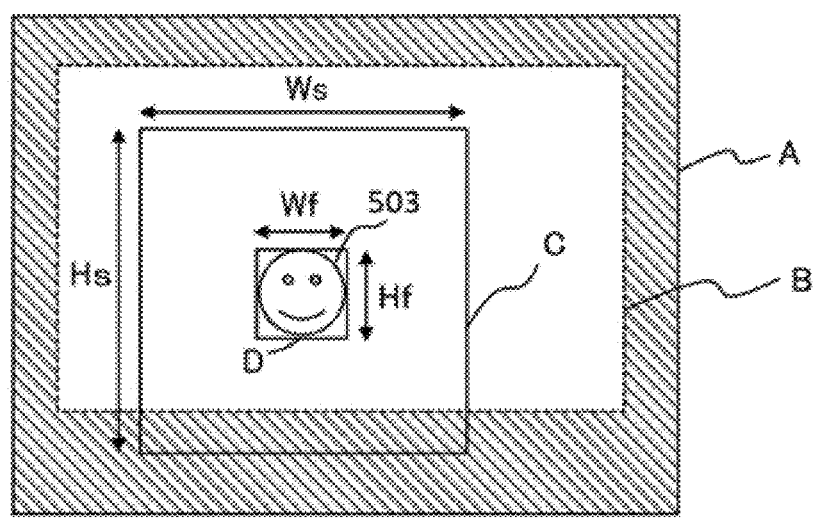
FIG. 4 is an explanatory diagram schematically illustrating a search area of the face detection device according to the first embodiment.

Next, the search area set by the search area setting unit 2 will be described. FIG. 4 is an explanatory diagram schematically illustrating a search area according to the first embodiment. The captured image is divided into an imaging area, a detection area, and a search area. In the example of FIG. 4, the imaging area, the detection area, the search area, and the face area are indicated by an area A, an area B, an area C, and an area D, respectively. The imaging area is the entire captured image acquired by the image acquisition unit 1. In addition, the detection area is an area in which the occupant is considered to normally be present in the captured image. Here, the detection area may be set in advance in consideration of a range in which the face of the occupant as the face detection target moves.

The search area is an area provided in the imaging area and set by the search area setting unit 2. When the operation of the face detection device 100 is started, that is, when the search for the face of the occupant is started, the search area setting unit 2 first sets a predetermined area such as the entire imaging area, the entire detection area, or a predefined area as the search area. Hereinafter, for the sake of description, the search area determined when the search for the face of the occupant is started is referred to as a search start area. The search start area is not different from the search area and is included in the search area. When the detection unit 3 succeeds in face detection, the search area setting unit 2 sets the search area so as to include at least a part of the face area on the basis of the coordinates and the center of the face area of the occupant, or the like.

The setting of the search area will be described. For example, when the face area detected by the detection unit 3 is a rectangle, the search area setting unit 2 sets the rectangle having a width Ws and a height Hs as the search area using the coordinates of the face area. Here, the size of Ws is equal to or larger than a width Wf of the face area detected by the detection unit 3, and the size of Hs is equal to or larger than a height Hf of the face area detected by the detection unit 3. For example, Ws and Hs are about 1.2 to 1.5 times as large as Wf and Hf, respectively. The search area may be set to include at least a part of the face area successfully detected by the detection unit 3. That is, the search area setting unit 2 may set the search area so as to include the entire face area detected by the detection unit 3, or may set the search area so that a part of the face area detected by the detection unit 3 goes out of the search area. The center of the search area is preferably matched with the center of the successfully detected face area. In this way, the range in which the face of the occupant is likely to be present can be set as the search area. Furthermore, the center of the search area may be shifted from the center of the face area as long as the face detection is not hindered.

Further, when the detection unit 3 has searched in the set search area (search area in n frames) and failed in face detection, the search area setting unit 2 sets again an area obtained by expanding the previously set search area as a new search area (search area in n+1 frames). Here, n is an integer greater than 0.

The expansion of the search area will be described. When the detection unit 3 has failed in face detection in the set search area, the search area setting unit 2 sets again an area having a width $Ws_{n+1}$ and a height $Hs_{n+1}$ as a search area so as to include at least a part of the search area having a width $Ws_n$ and a height $Hs_n$ set last time, and expands the search area. That is, the search area setting unit 2 may expand the search area so that a newly set search area includes the entire search area searched by the detection unit 3, or may expand the search area so that a part of the search area searched by the detection unit 3 goes out of the newly set search area. Here, $Ws_{n+1}$ is greater than $Ws_n$, and $Hs_{n+1}$ is greater than $H_{Sn}$.

For example, $Ws_{n+1}$ and $Hs_{n+1}$ are obtained by multiplying Wf and Hf by predetermined magnifications, respectively. When the expansion of the search area is repeated, Wf and Hf may be multiplied by magnifications larger than the previous magnifications, respectively. In addition, $Ws_{n+1}$ and $Hs_{n+1}$ may be expanded by multiplying $Ws_n$ and $Hs_n$ by predetermined magnifications, respectively. In this case, the search area may be expanded using the coordinates of the previously set search area. Further, the search area may be expanded by a predetermined dimension, for example, by adding a constant to at least one of $Ws_{n+1}$ and $Hs_{n+1}$ after being expanded by a predetermined magnification. Here, the predetermined magnification is about 1.5 to 3 times. In this way, by expanding the search area using at least one of the dimension of the previously detected face area and the dimension of the previously set search area, it is possible to suppress the search area from being excessively expanded with respect to the face area.

The center of the newly set expanded search area is preferably matched with the center of the previously detected face area. In this way, the search area setting unit 2 can expand the search area at a position where the face of the occupant is likely to be present. Here, the center of the newly set expanded search area may be matched with the center of the previously set search area. In addition, the center of the newly set search area may deviate from the center of the face area successfully detected by the detection unit 3 or the center of the search area previously searched by the detection unit 3 as long as it is within a range that does not hinder face detection.

When the detection of the face of the occupant fails, the search area setting unit 2 does not need to match the center of the face area successfully detected by the detection unit 3 or the center of the search area previously searched by the detection unit 3 with the center of the newly set search area. In this way, the search area can be expanded while being moved.

Further, when the detection unit 3 has failed in face detection in the set search area, the search area setting unit 2 may maintain or change the search area. When maintaining the search area, the search area setting unit 2 does not expand the search area and sets again the search area previously searched by the detection unit 3 as the search area. When changing the search area, for example, the search area setting unit 2 changes the search area to a predetermined area defined as a search start area. In addition, the search area may be changed to an area different from the predetermined area defined as the search start area.

Here, in a case where the search area has been set in such a manner that a part of the search area is included in the outside of the detection area (area indicated by hatching in FIG. 4), and the detection unit 3 has detected a face outside the detection area, the detection determination unit 4 preferably determines that the detection unit 3 has failed in face detection. In this case, when the detection unit 3 has detected at least a part of the face of the occupant outside the detection area, the detection determination unit 4 may determine that the detection of the face of the occupant has failed. For example, when the detection area is set to a range not including the side window of the vehicle, the detection unit 3 can be prevented from erroneously detecting the face of a person outside the vehicle, the face of an occupant reflected in the side window, and the like, and the detection accuracy is improved.

Figure 5:
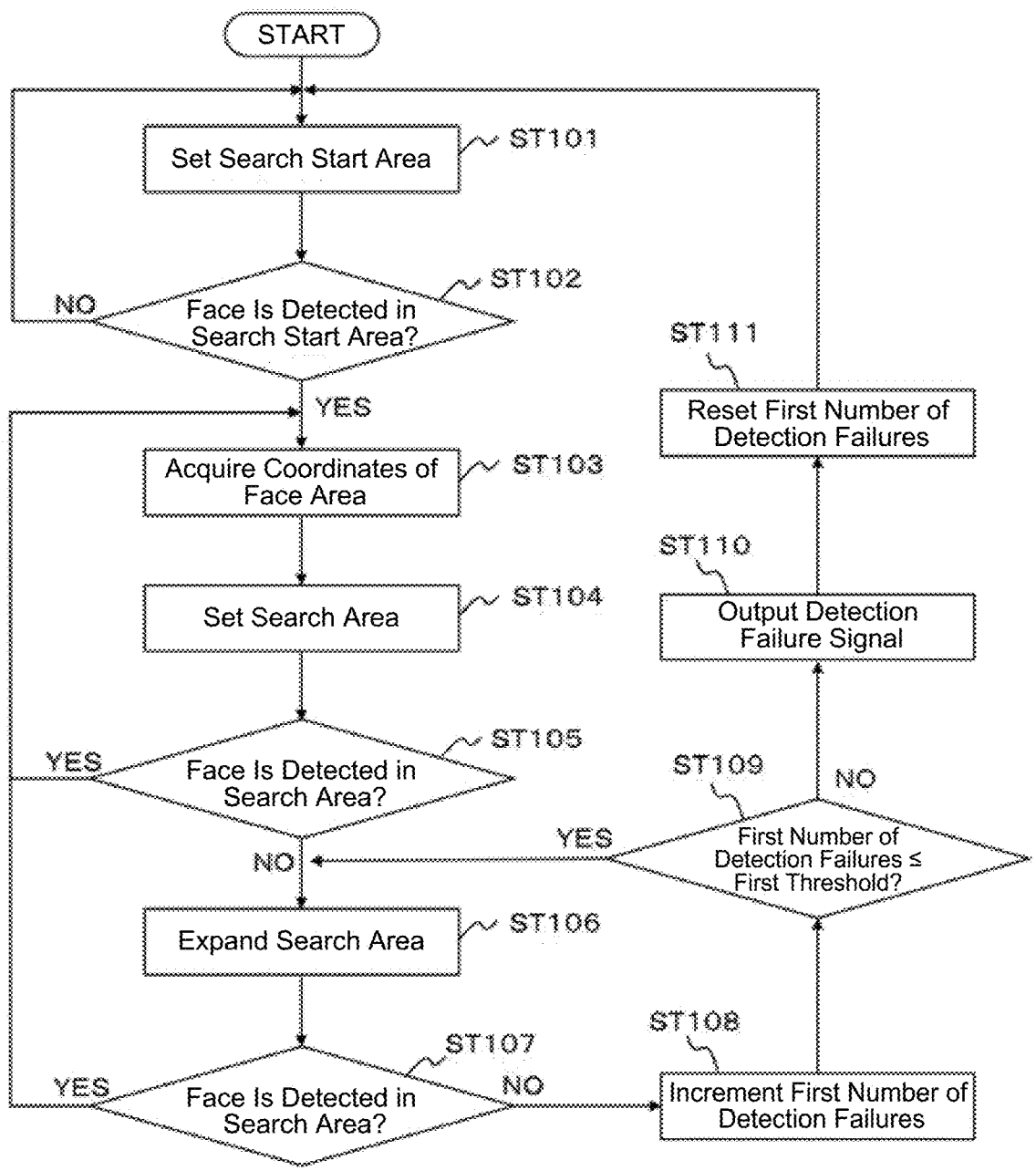
FIG. 5 is a flowchart illustrating an operation example of the face detection device according to the first embodiment.

Hereinafter, the operation of the face detection device 100 will be described. FIG. 5 is a flowchart illustrating an operation example of the face detection device 100 according to the first embodiment. In addition, although the flowchart of FIG. 5 does not illustrate processing of ending the operation of the face detection device 100, the face detection device 100 ends the operation when receiving a command to end the operation of face detection from the control device 300.

First, the search area setting unit 2 sets a predetermined area as a search start area in the captured image acquired by the image acquisition unit 1 (ST101).

Next, the detection unit 3 searches for the face of the occupant in the search start area (ST102). Here, when the detection determination unit 4 determines that the detection unit 3 has failed in face detection (ST102; NO), the detection unit 3 again searches for the face of the occupant in the search start area. That is, the detection unit 3 repeats the search for the face of the occupant until the face detection succeeds in the search start area.

When the detection determination unit 4 determines that the detection unit 3 has succeeded in face detection in the search start area (ST102; YES), the search area setting unit 2 acquires the coordinates of the face area from the detection unit 3 (ST103).

Then, the search area setting unit 2 sets a search area using the acquired coordinates of the face area (ST104). For example, the search area setting unit 2 sets the search area on the basis of the face area so as to include at least a part of the face area detected by the detection unit 3.

The detection unit 3 continues searching for the face of the occupant in the set search area (ST105). When having succeeded in face detection in the search area (ST105; YES), the face detection device 100 repeats the processing of steps ST103 to ST105 described above.

On the other hand, when the detection determination unit 4 determines that the detection unit 3 has failed in face detection in the search area (ST105; NO), the search area setting unit 2 expands the search area (ST106). The search area setting unit 2 sets the coordinates of the search area so as to include at least a part of the search area previously searched by the detection unit 3, and expands the search area. Here, the search area is preferably expanded to include all the search areas searched by the detection unit 3 in the processing of step ST105.

Then, the detection unit 3 searches for the face of the occupant in the expanded search area (ST107). When the detection determination unit 4 determines that the detection unit 3 has succeeded in face detection in the expanded search area (ST107; YES), the process proceeds to step ST103, and the face detection device 100 repeats the processing of steps ST103 to ST105 described above.

On the other hand, when the detection determination unit 4 determines that the detection unit 3 has failed in face detection in the expanded search area (ST107; NO), the process proceeds to step ST108 described below.

The number of times that the detection unit 3 has failed in face detection is recorded by the detection determination unit 4. The detection determination unit 4 increments and records the number of times of determination that face detection has failed in the search area (hereinafter, referred to as a first number of detection failures) (ST108). Furthermore, the first number of detection failures is provided with a threshold (hereinafter, referred to as a first threshold) in advance.

When the detection determination unit 4 determines whether or not the first number of detection failures is equal to or less than the first threshold (ST109) and the detection determination unit 4 determines that the first number of detection failures exceeds the first threshold (ST109; NO), a detection failure signal indicating that the first number of detection failures exceeds the first threshold is output from the output unit 5 to the control device 300 (ST110). Here, the first threshold is an integer greater than 0.

After the detection determination unit 4 outputs the detection failure signal, the first number of detection failures is reset (ST111), and the search area setting unit 2 changes the search area to a predetermined area defined as a search start area. Then, the detection unit 3 again searches for the face of the occupant in the search start area. On the other hand, when the first number of detection failures is equal to or less than the first threshold (ST109; YES), the search area setting unit 2 expands the search area until the face detection is successful, and repeats the expansion of the search area until the first number of detection failures exceeds the first threshold. Here, in addition to the processing of step ST111, the first number of detection failures is also reset when the detection determination unit 4 determines that the detection unit 3 has succeeded in face detection.

That is, when the detection determination unit 4 determines that the detection unit 3 has failed in face detection in the set search area, the search area setting unit 2 expands the search area with reference to the search area in which the face detection has been successful last time, and repeats the expansion of the search area a predetermined number of times until the detection unit 3 succeeds in the face detection.

As described above, the image acquisition unit 1 to acquire the captured image, the search area setting unit 2 to set the search area in the captured image acquired by the image acquisition unit 1, the detection unit 3 to search the search area and detect the face of the occupant, and the detection determination unit 4 to determine whether or not the detection unit 3 has succeeded in detecting the face of the occupant are included, and when it is determined that the detection of the face of the occupant has failed, the search area setting unit 2 expands the search area searched by the detection unit 3, thereby expanding the range of searching for the face of the occupant and detecting the face of the occupant again even when the detection of the face of the occupant has failed, so that the detection accuracy is improved. Furthermore, in a case where the imaging range is wide, even if the face of the occupant moves out of the search area, the search area is expanded and the face of the occupant is searched again. Therefore, the processing load is reduced as compared with a case where the entire imaging area is searched.

Note that, in the first embodiment, an example in which the face area detected by the detection unit 3 is a rectangle has been described. However, the face area detected by the detection unit 3 may have a shape such as an oval. In this case, for example, the flatness, the length of the major axis, the length of the minor axis, the center of the oval, and the like may be used as the information related to the face area detected by the detection unit 3.

In addition, in the first embodiment, an example has been described in which the search area setting unit 2 expands the search area by referring to at least one of the face area previously detected by the detection unit 3 and the search area searched by the detection unit 3. However, the search area may be expanded by referring to at least one of the face area detected by the detection unit 3 and the search area searched by the detection unit 3 by tracing back several past frames.

In the first embodiment, the example in which the face area is detected on the basis of a contour of the face of the occupant is described. Alternatively, the face area may be detected on the basis of an element of the face of the occupant such as an eye, a nose, a mouth, and a cheek. In this case, the detection unit 3 may detect the face area on the basis of the size of each element and the relative position of each element. In this way, when the face direction of the occupant changes, the search area setting unit 2 can set the search area in accordance with the face direction.

Further, in the first embodiment, the example in which the signal is output to the control device 300 when the face detection has failed has been described. However, even when the face detection has succeeded, a signal indicating that the face detection has succeeded, information related to the detected face area, and the like may be output to the control device 300.

Furthermore, in the first embodiment, the example has been described in which the occupants 503 and 504 seated on the driver's seat 501 and the passenger seat 502, respectively, are simultaneously imaged by the imaging device 200. However, the occupants 503 and 504 seated on the driver's seat 501 and the passenger seat 502 may be separately imaged by the imaging device 200. In this case, an imaging device 200 that images the occupant 503 seated on the driver's seat 501 and an imaging device 200 that images the occupant 504 seated on the passenger seat 502 may be separately provided.

Second Embodiment

A face detection device 100 according to a second embodiment includes an image acquisition unit 1, a search area setting unit 2, a detection unit 3, and a detection determination unit 4 as in the first embodiment. The present embodiment is different from the first embodiment in a processing operation of the face detection device 100 in that face detection is performed using a first area to be described later. The same components as those in the first embodiment are denoted by the same reference numerals, and the description thereof will be omitted.

Figure 6A:
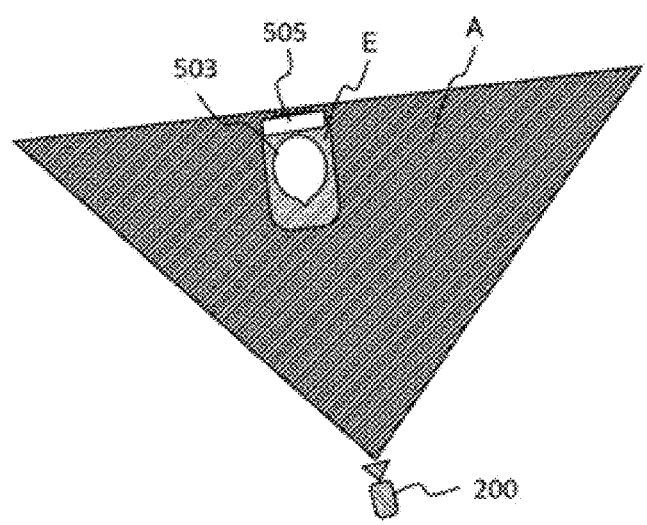
FIGS. 6A and 6B are explanatory diagrams of a first area according to a second embodiment.
Figure 6B:
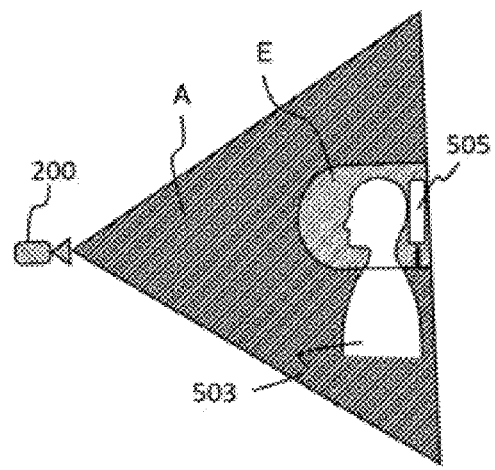

FIG. 6 is an explanatory diagram of a first area according to the second embodiment. FIG. 6A is a diagram of the inside of the vehicle imaged by the imaging device 200 as viewed from above, and FIG. 6B is a diagram of the inside of the vehicle imaged by the imaging device 200 as viewed from the side, and a first area to be described later is indicated by an area E.

The first area is an area set on the basis of the position of the driver's seat and the position of the imaging device 200 for each vehicle type, for example, an area provided around a headrest 505. The first area is set in consideration of an adjustment width of the seat of the driver's seat 501 in the front-rear direction, an adjustment width of the inclination of the seat of the driver's seat 501, and an adjustment width of the headrest 505 of the driver's seat 501 in the vertical direction. In addition, the first area may be set in consideration of an average seat position of the driver's seat 501, an average seating height of the driver, or a range imaged when a general driver performs a normal driving operation. Here, the first area is preferably an area including the entire headrest 505 of the driver's seat 501.

The first area may be set for each of the passenger seat 502 and the rear seat. In this case, in consideration of the adjustment width of each seat in the front-rear direction, the adjustment width of the inclination of each seat, and the adjustment width of the headrest 505 in the vertical direction, an average seat position of occupants, an average seating height of occupants, or a range in which a general occupant is normally imaged may be set as the first area.

Figure 7:
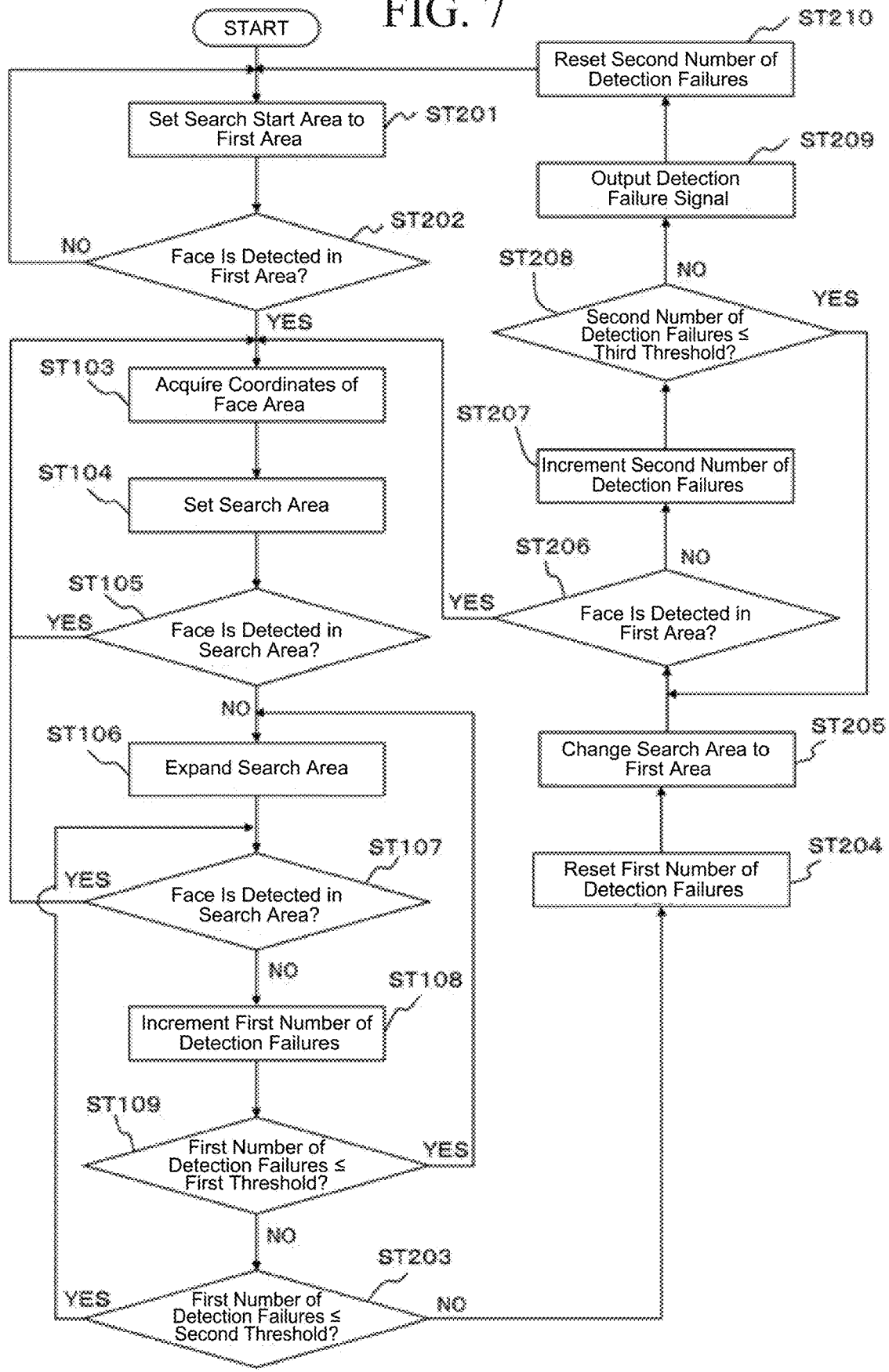
FIG. 7 is a flowchart illustrating an operation example of a face detection device according to the second embodiment.

Hereinafter, the operation of the face detection device 100 will be described. FIG. 7 is a flowchart illustrating an operation example of the face detection device 100 according to the second embodiment. Hereinafter, the same steps as those in the processing of the face detection device 100 according to the first embodiment are denoted by the same reference numerals as those illustrated in FIG. 5, and the description thereof will be omitted or simplified. In addition, although the flowchart of FIG. 7 does not illustrate processing of ending the operation of the face detection device 100, the face detection device 100 ends the operation when receiving a command to end the face detection operation from the control device 300.

First, the search area setting unit 2 sets the first area as a search start area in the captured image acquired by the image acquisition unit 1 (ST201). Then, the detection unit 3 searches for the face of the occupant in the first area (ST202). When the detection determination unit 4 determines that the detection unit 3 has failed in face detection in the first area (ST202; NO), the detection unit 3 again searches for the face of the occupant in the first area. That is, the detection unit 3 searches the first area until the face detection succeeds in the first area.

When the detection determination unit 4 determines that the detection unit 3 has succeeded in face detection in the first area (ST202; YES), the search area setting unit 2 acquires the coordinates of the face area from the detection unit 3 (ST103), sets the search area on the basis of the coordinates of the face area (ST104), and proceeds to processing of step ST105.

In step ST105, when having succeeded in face detection in the search area (ST105; YES), the face detection device 100 repeats the processing of steps ST103 to ST104 described above. On the other hand, in step ST105, if face detection has failed in the search area (ST105; NO), the search area setting unit 2 expands the search area (ST106), and the detection unit 3 searches for the face of the occupant again in the expanded search area (ST107).

In step ST107, if the face detection is successful (ST107; YES), the process proceeds to the processing of step ST103, and the processing of steps ST103 to ST104 described above is repeated.

Further, in step ST107, if the face detection has failed (ST107; NO), the detection determination unit 4 increments and records the first number of detection failures (ST108). When it is determined in the processing of step ST109 that the first number of detection failures is equal to or less than the first threshold (ST109; YES), the process proceeds to step ST106. On the other hand, when it is determined that the first number of detection failures has exceeded the first threshold (ST109; NO), the process proceeds to step ST203 described below.

If it is determined in step ST109 that the first number of detection failures has exceeded the first threshold (ST109; NO), the detection determination unit 4 determines whether or not the first number of detection failures has exceeded a second threshold (ST203). Here, the second threshold is an integer larger than the first threshold.

When the detection determination unit 4 determines that the first number of detection failures is equal to or less than the second threshold (ST203; YES), the process proceeds to step ST107, and the face of the occupant is searched for a predetermined number of times in the expanded search area. That is, when the detection determination unit 4 determines that the first number of detection failures is equal to or less than the second threshold, the detection unit 3 searches for the face of the occupant in the search area maintained without being expanded by the search area setting unit 2.

On the other hand, when the detection determination unit 4 determines that the first number of detection failures has exceeded the second threshold (ST203; NO), the detection determination unit 4 resets the first number of detection failures (ST204). Then, upon receiving a signal indicating that the first number of detection failures has been reset from the detection determination unit 4, the search area setting unit 2 changes the search area to the first area (ST205).

Next, the detection unit 3 searches for the face of the occupant in the first area (ST206). When the detection determination unit 4 determines that the face of the occupant has been successfully detected in the first area (ST206; YES), the process proceeds to step ST103, and the search area setting unit 2 acquires the coordinates of the face area detected by the detection unit 3 and sets the search area.

When the detection determination unit 4 determines that the face detection has failed in the first area (ST206; NO), the detection determination unit 4 increments and records the number of detection failures of the face of the occupant (ST207) as a second number of detection failures. Then, the detection determination unit 4 determines whether or not the second number of detection failures is equal to or less than a predefined third threshold (ST208). When the detection determination unit 4 determines that the second number of detection failures is equal to or less than the third threshold (ST208; YES), the process proceeds to step ST206, and the detection unit 3 searches for the face of the occupant in the first area. Here, the third threshold is an integer greater than 0.

On the other hand, when the detection determination unit 4 determines that the second number of detection failures has exceeded the third threshold (ST208; NO), the output unit 5 outputs a detection failure signal indicating that the second number of detection failures has exceeded the third threshold to the control device 300 (ST209).

After outputting the detection failure signal, the detection determination unit 4 resets the second number of detection failures (ST210), proceeds to the processing of step ST201, and the search area setting unit 2 maintains the search area in the first area. Then, the detection unit 3 again searches for the face of the occupant in the first area. Here, in addition to the processing of steps ST204 and ST210, the first number of detection failures and the second number of detection failures are also reset when the detection determination unit 4 determines that the detection unit 3 has succeeded in face detection.

That is, when the detection determination unit 4 determines that the detection unit 3 has failed in detecting the face of the occupant, the search area setting unit 2 expands the search area. When the detection unit 3 has failed in detecting the face of the occupant a predetermined number of times, the search area setting unit 2 changes the search area to the first area. In this way, even when the detection of the face of the occupant has failed, the search area is expanded to detect the face of the occupant again, and the search area is changed to the first area provided in the headrest of the seat on which the occupant is seated, so that the area in which the face of the occupant to be detected is highly likely to be present can be searched again. Therefore, the detection accuracy is improved.

Furthermore, in the present embodiment, an example in which the first area is set as the search start area has been described, but any one of the entire imaging area, the entire detection area, and a predefined area may be set as the search start area.

In the present embodiment, the example has been described in which the search area setting unit 2 changes the search area to the first area when the detection determination unit 4 determines that the first number of detection failures has exceeded the second threshold. However, the search area setting unit 2 may change the search area to the first area when the detection determination unit 4 determines that the first number of detection failures has exceeded the first threshold. In this case, the second threshold is not provided, and the processing of step ST203 may be omitted.

Third Embodiment

Figure 8:
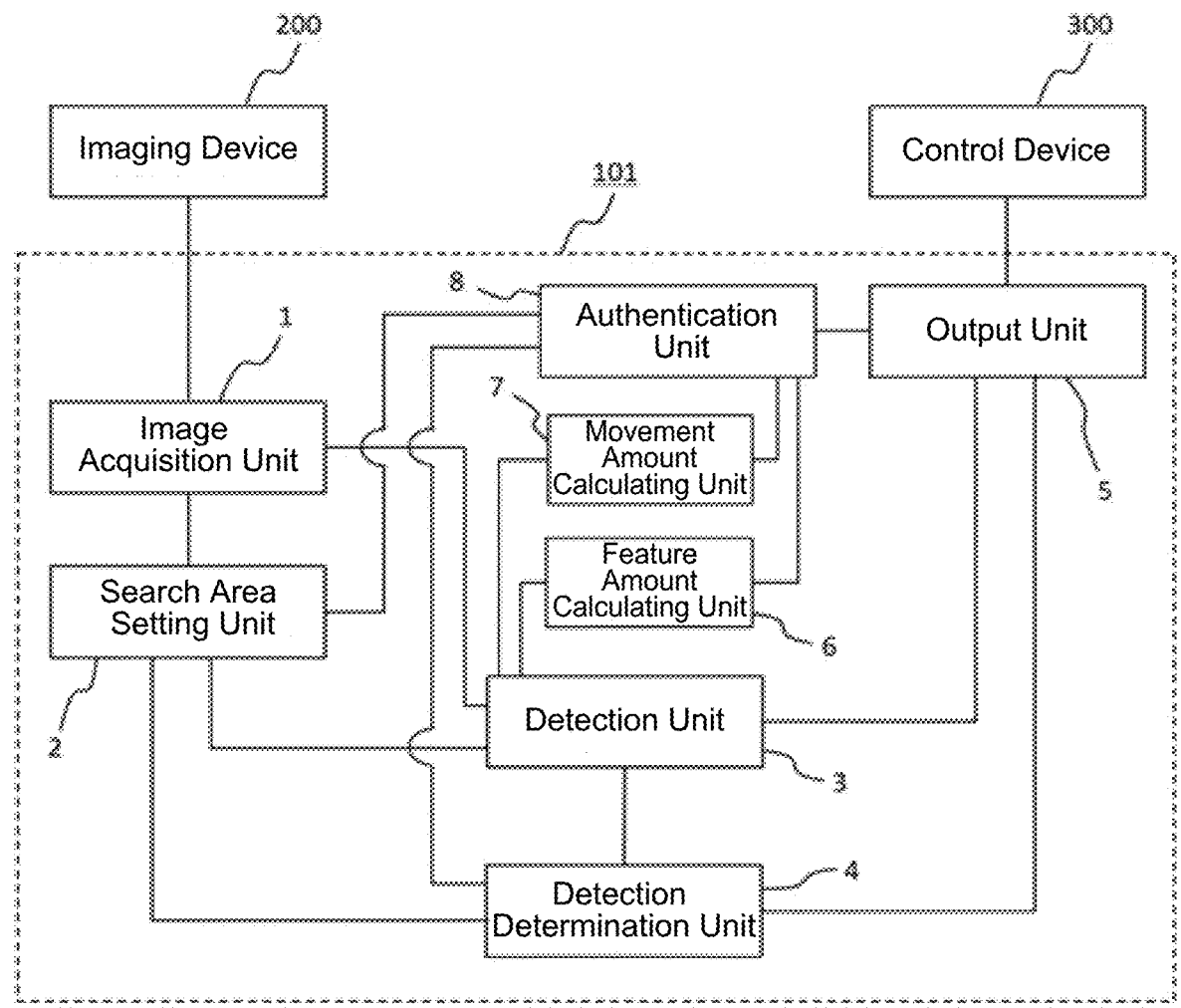
FIG. 8 is a block diagram schematically illustrating a configuration of a face detection device according to a third embodiment.

FIG. 8 is a block diagram schematically illustrating a configuration of a face detection device 101 according to a third embodiment. Similarly to the first embodiment, the face detection device 101 according to the present embodiment includes an image acquisition unit 1, a search area setting unit 2, a detection unit 3, and a detection determination unit 4. The present embodiment is different from the first embodiment in that it includes a feature amount calculating unit 6, a movement amount calculating unit 7, and an authentication unit 8, and the authentication unit 8 authenticates the occupant detected by the detection unit 3. The same components as those of the first embodiment are denoted by the same reference numerals, and the description thereof will be omitted.

The feature amount calculating unit 6 acquires feature information of the face of the occupant detected by the detection unit 3, and calculates and records the feature amount of the face of the occupant. The feature amount is, for example, a size of each element such as an eye, a nose, a mouth, and a cheek, a distance between a contour and each element, a distance between each elements, and the like after the size of the face is normalized, and is a value unique to the occupant. In addition, the feature amount calculating unit 6 calculates a change amount between the feature amount of the face of the occupant previously detected by the detection unit 3 and the newly detected feature amount of the face of the occupant. Here, the change amount of the feature amount is, for example, a difference or a change rate between the feature amount of the face of the previously detected occupant and the feature amount of the face of the newly detected occupant.

The movement amount calculating unit 7 calculates the movement amount between the face of the occupant previously detected by the detection unit 3 and the face of the newly detected occupant. For example, in a case where the face area is a rectangle, the movement amount is a movement amount of a center of the rectangle, a center of each side of the rectangle, a vertex of the rectangle, and the like, and also includes a change amount of an area of the face area accompanying a change in the size of the face area.

The authentication unit 8 authenticates the occupant by the detection unit 3 determining whether or not an occupant whose face has been previously successfully detected matches an occupant whose face has been newly successfully detected. Hereinafter, determining whether or not the previously detected occupant matches the newly detected occupant is referred to as face authentication. Various known algorithms can be used for the face authentication, and a detailed description of these algorithms will be omitted.

For example, the authentication unit 8 compares, between the face of the previously detected occupant and the face of the newly detected occupant, the change amount of the feature amount calculated by the feature amount calculating unit 6 and the movement amount calculated by the movement amount calculating unit 7 with an authentication threshold, and determines whether or not the face authentication is successful. Then, the authentication unit 8 outputs a determination result as to whether or not the face authentication is successful to the search area setting unit 2. The authentication threshold is a threshold used for face authentication which is set after the operation of the face detection device 101 is started or which is preset. Here, when the feature amount and the movement amount exceed the authentication threshold, the authentication unit 8 determines that the face authentication has failed. Further, the authentication unit 8 increments and records the number of times of determination that the face authentication has failed (hereinafter, referred to as a number of authentication failures). Then, when the authentication unit 8 determines that the face authentication has failed, the search area setting unit 2 expands, maintains, or changes the search area.

In this way, the feature amount calculating unit 6 to calculate the feature amount of the face of the occupant, the movement amount calculating unit 7 to calculate the movement amount of the face of the occupant, and the authentication unit 8 to perform face authentication using the feature amount and the movement amount calculated by the feature amount calculating unit 6 and the movement amount calculating unit 7, respectively, are provided, and thus it is possible to determine whether or not the occupants detected by the detection unit 3 match each other.

Figure 9:
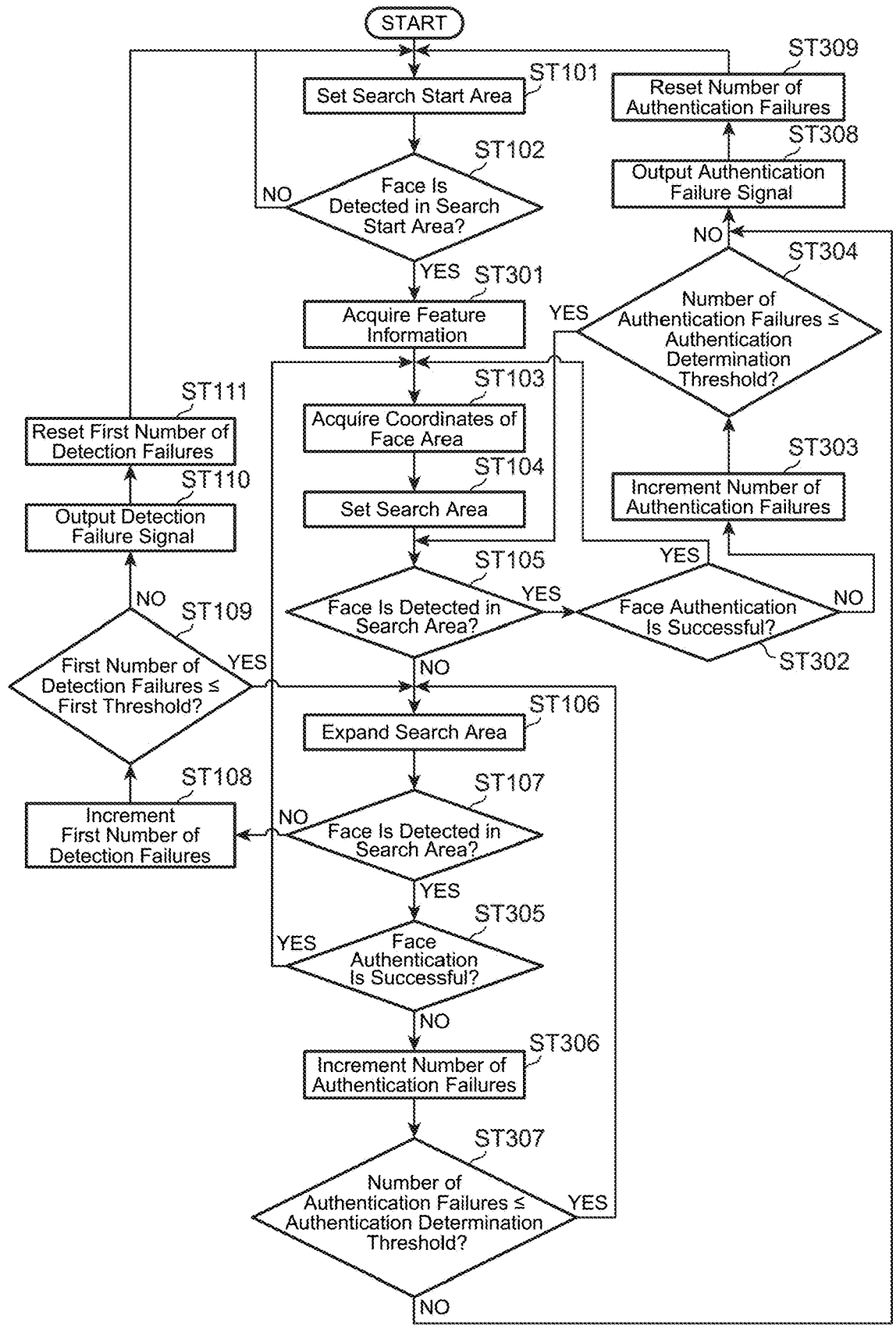
FIG. 9 is a flowchart illustrating an operation example of the face detection device according to the third embodiment.

Hereinafter, the operation of the face detection device 101 will be described. FIG. 9 is a flowchart illustrating an operation example of the face detection device 101 according to the third embodiment. Hereinafter, the same steps as those in the processing of the face detection device 100 according to the first embodiment are denoted by the same reference numerals as those illustrated in FIG. 5, and the description thereof will be omitted or simplified. In addition, although the flowchart of FIG. 9 does not illustrate processing of ending the operation of the face detection device 101, the face detection device 101 ends the operation when receiving a command to end the face detection operation from the control device 300.

First, in the processing of steps ST101 to ST102, the detection unit 3 searches for the face of the occupant until the face of the occupant is successfully detected in the search start area. When the detection determination unit 4 determines that the detection unit 3 has succeeded in detecting the face of the occupant (ST102; YES), the feature amount calculating unit 6 acquires the feature information of the face of the occupant detected by the detection unit 3, and calculates and records the feature amount (ST301).

In addition, the search area setting unit 2 acquires the coordinates of the face area from the detection unit 3 (ST103) and sets the search area (ST104). Then, the detection unit 3 searches for the face of the occupant in the set search area (ST105).

When the detection determination unit 4 determines that the detection unit 3 has succeeded in face detection (ST105; YES), the detection unit 3 outputs feature information of the detected face of the occupant and the coordinates of the face area to the feature amount calculating unit 6 and the movement amount calculating unit 7, respectively. Further, the feature amount calculating unit 6 calculates the feature amount of the successfully detected face of the occupant, and the movement amount calculating unit 7 calculates the movement amount between the face area of the occupant successfully detected previously and the face area of the occupant successfully detected newly. Then, the feature amount calculating unit 6 and the movement amount calculating unit 7 output the feature amount and the movement amount, respectively, to the authentication unit 8. Further, the authentication unit 8 performs face authentication using the feature amount, the movement amount, and the authentication threshold (ST302).

When the authentication unit 8 has determined that the previously detected occupant matches the newly detected occupant, that is, when the face authentication has succeeded (ST302; YES), the authentication unit 8 outputs a determination result indicating that the face authentication has succeeded to the search area setting unit 2. Then, the process proceeds to step ST103, the search area setting unit 2 sets the search area using the coordinates of the face area detected by the detection unit 3, and the detection unit 3 continues searching for the face of the occupant in the set search area.

On the other hand, when the authentication unit 8 determines that the previously detected occupant does not match the newly detected occupant, that is, when the face authentication fails (ST302; NO), the process proceeds to step ST303 described below.

The number of failures in the face authentication is recorded by the authentication unit 8. The authentication unit 8 increments and records the number of authentication failures (ST303). Further, the number of authentication failures is provided with a threshold (hereinafter, referred to as an authentication determination threshold) in advance.

The authentication unit 8 determines whether or not the number of authentication failures is equal to or less than the authentication determination threshold (ST304), and when the authentication unit 8 determines that the number of authentication failures has exceeded the authentication determination threshold (ST304; NO), an authentication failure signal indicating that the number of authentication failures has exceeded the authentication determination threshold is output from the output unit 5 to the control device 300 (ST308). Here, the authentication determination threshold is an integer greater than 0.

After the authentication failure signal is output, the number of authentication failures is reset (ST309), and the search area setting unit 2 changes the search area to a predetermined area defined as a search start area (ST101). Then, the detection unit 3 again searches for the face of the occupant in the search start area (ST102).

On the other hand, when the authentication unit 8 determines that the number of authentication failures is equal to or less than the authentication determination threshold (ST304; YES), the process proceeds to step ST105, and the detection unit 3 again searches the search area maintained from the search area set by the search area setting unit 2 in the processing of step ST104.

If the detection determination unit 4 determines that the detection unit 3 has failed in face detection in the processing of step ST105 (ST105; NO), the process proceeds to step ST106.

The search area is expanded in step ST106, and the detection unit 3 searches for the face of the occupant in the expanded face area (ST107). Then, in a case where face detection has failed in the processing of step ST107 (ST107; NO), the processing of steps ST108 to ST111 is performed, and the expansion of the search area and the searching for the face of the occupant are repeated a predetermined number of times.

On the other hand, in a case where the face detection is successful in the processing of step ST107 (ST107; YES), the authentication unit 8 performs face authentication of the occupant detected by the detection unit 3, similarly to the processing of step ST302 (ST305).

When the face authentication of the occupant is successful (ST305; YES), the process proceeds to step ST103, and searching for the face of the occupant is continued. When the face authentication of the occupant fails (ST305; NO), the number of authentication failures is incremented and recorded (ST306).

When the number of authentication failures is equal to or less than the authentication determination threshold (ST307; YES), the process proceeds to step ST106, the processing of steps ST106 to ST107 and ST305 are performed, and the expansion of the search area, the search of the search area, and the face authentication of the detected occupant are repeated. When the number of authentication failures has exceeded the authentication determination threshold (ST307; NO), an authentication failure signal indicating that the number of authentication failures has exceeded the authentication determination threshold is output from the output unit 5 to the control device 300 (ST308).

After the authentication failure signal is output, the number of authentication failures is reset (ST309), and the search area setting unit 2 changes the search area to a predetermined area defined as a search start area (ST101). Then, the detection unit 3 again searches for the face of the occupant in the search start area (ST102). Here, in addition to the processing of step ST111, the first number of detection failures is also reset when the detection determination unit 4 determines that face detection has succeeded. In addition to the processing of step ST309, the number of authentication failures is also reset when the authentication unit 8 determines that the face authentication is successful.

That is, when the detection unit 3 detects the face of the occupant, the authentication unit 8 determines whether or not the occupant detected from the feature amount and the movement amount of the face of the occupant matches the occupant detected at the start of face detection. When the authentication unit 8 determines that the detected occupants do not match, the search area setting unit 2 expands, maintains, or changes the search area. Further, when the face authentication of the occupant fails a predetermined number of times, the search area setting unit 2 changes the search area. In this way, when the detection of the face of the occupant fails, the range of searching for the face of the occupant is expanded, and the face of the occupant is detected again, so that the detection accuracy is improved. Furthermore, even when the face of the previously detected occupant does not match the face of the newly detected occupant due to, for example, a face of an occupant other than the occupant to be detected being included in the search area, the search area is expanded, maintained, or changed, and the face of the occupant is searched for again, so that the detection accuracy of the face of the occupant can be ensured.

Note that, in the present embodiment, the example has been described in which the search area is not expanded during the processing of step ST304 and step ST105, that is, when the face of the occupant is detected and it is determined that the occupants do not match, but the search area may be expanded during the processing of step ST304 and step ST105.

Furthermore, in the present embodiment, the example has been described in which the movement amount of the face of the occupant is calculated using each side of the rectangle, but the same applies to a case other than the rectangle. For example, when the face area is an oval, the movement amount may be calculated on the basis of the change amount of the center, the minor axis, the major axis, and the like.

Furthermore, in the present embodiment, the example has been described in which the authentication unit 8 performs the face authentication using the feature amount and the movement amount, but the face authentication may be performed using either the feature amount or the movement amount. In this case, an authentication threshold may be provided for each of the feature amount and the movement amount, and the authentication unit 8 may compare one of the feature amount and the movement amount with the authentication threshold. When the authentication threshold is not provided for each of the feature amount and the movement amount, the feature amount and the movement amount may be normalized and compared with the authentication threshold.

Note that, although the example of detecting one occupant has been described in the first to third embodiments, the same applies to a case of detecting an occupant other than the occupant 503 and a case of detecting a plurality of occupants using the face detection device 100, 101 in the present disclosure. When a plurality of occupants are detected, the detection may be performed for the plurality of occupants.

In the first to third embodiments, the example has been described in which when the detection of the face of the occupant fails, the search area setting unit 2 expands or maintains the search area on the basis of the center of the previously searched search area. However, the search area may be expanded or maintained while moving the center of the search area. For example, in a case where the detection unit 3 has failed in face detection by recording the center of the face area detected by the detection unit 3 in the past several frames in a recording unit or the like (not illustrated) and specifying the direction in which the face of the occupant has moved, the search area setting unit 2 can immediately detect the face of the occupant by moving the center in the specified moving direction to expand or maintain the search area.

Furthermore, in the first to third embodiments, the example has been described in which the search area setting unit 2 expands the width and the height of the search area previously searched by the detection unit 3 at a predetermined magnification. However, the search area may be expanded using at least one of the width and the height of the previously searched search area. In addition, the search area may be expanded using at least one of the width and the height of the face area acquired from the detection unit 3. In this case, at least one of the width and the height of the previously searched search area may be expanded at a predetermined magnification. Furthermore, the magnification to be expanded may be changed in accordance with the number of detection failures of the face of the occupant by the detection unit 3 and the size of the face area acquired from the detection unit 3.

In the first to third embodiments, the example has been described in which the search area setting unit 2 does not expand the search area when the detection unit 3 has failed in detecting the face of the occupant in the search start area. However, the search area may be expanded even when the detection unit 3 has failed in detecting the face of the occupant in the search start area. That is, even in a case where the face detection device 100, 101 starts face detection and cannot detect the face of the occupant even once, the search area setting unit 2 may expand the search area.

In addition, each embodiment disclosed in the present specification can be freely combined within the scope thereof, and each embodiment can be appropriately modified or omitted.

REFERENCE SIGNS LIST

1: image acquisition unit, 2: search area setting unit, 3: detection unit, 4: detection determination unit, 5: output unit, 6: feature amount calculating unit, 7: movement amount calculating unit, 8: authentication unit, 100, 101: face detection device, 100*a*: processing circuit, 100*b*: processor, 100*c*: memory, 200: imaging device, 300: control device, 501: driver's seat, 502: passenger seat, 503, 504: occupant, 505: headrest

The invention claimed is:

1. A face detection device, comprising:
   processing circuitry configured to
   acquire, from an imaging device mounted on a vehicle and imaging an at least one occupant inside the vehicle, a captured image in which the at least one occupant is imaged;
   set a search area in which a face of the at least one occupant is searched in the acquired captured image;
   search the search area and detect the face of the at least one occupant; and
   determine whether or not the detection of the face of the at least one occupant has succeeded, wherein
   the processing circuitry expands the search area when determining that the detection of the face of the at least one occupant has failed,
   the processing circuitry determines whether or not a first number of detection failures in which the detection of the face of the at least one occupant is determined to be failure is equal to or less than a first threshold, and
   the processing circuitry
      expands the search area when determining that the first number of detection failures is equal to or less than the first threshold, and
      maintains or changes the search area when determining that the first number of detection failures exceeds the first threshold.

2. The face detection device according to claim 1, wherein when determining that the detection of the face of the at least one occupant has failed, the processing circuitry expands the search area by using coordinates of a face area including the face of the at least one occupant.

3. The face detection device according to claim 1, wherein, when starting a search for the face of the at least one occupant, the processing circuitry sets the search area in a first area provided in a headrest of a seat on which the at least one occupant is seated.

4. The face detection device according to claim 1, wherein the processing circuitry changes the search area to the first area when determining that the first number of detection failures exceeds the first threshold.

5. The face detection device according to claim 1, wherein the processing circuitry maintains the search area when determining that the first number of detection failures exceeds the first threshold and is equal to or less than a second threshold larger than the first threshold, and
   changes the search area when determining that the first number of detection failures exceeds the second threshold.

6. The face detection device according to claim 5, wherein the processing circuitry changes the search area to the first area when determining that the first number of detection failures exceeds the second threshold.

7. The face detection device according to claim 1,
   wherein the at least one occupant comprises a plurality of occupants, and
   the processing circuitry is further configured to
   calculate a feature amount of the face of the at least one occupant from an element of the face of the at least one occupant having been detected;
   determine whether or not the detected occupants match each other by using the calculated feature amount; and
   expand the search area when determining that the detected occupants do not match.

8. The face detection device according to claim 7,
   wherein the processing circuitry is further configured to calculate a movement amount of the face of the at least one occupant having been detected, and
   wherein the processing circuitry determines whether or not the detected occupants match each other by using the calculated movement amount.

9. The face detection device according to claim 7,
   wherein the processing circuitry determines whether or not a number of authentication failures is equal to or less than an authentication determination threshold when determining that the detected occupants do not match each other, and
   the processing circuitry expands the search area when determining that the number of authentication failures is equal to or less than the authentication determination threshold, and changes the search area when determining that the number of authentication failures exceeds the authentication determination threshold.

10. The face detection device according to claim 1,
    wherein the processing circuitry acquires a center of the face area when determining that the detection of the face of the at least one occupant has succeeded, and
    when determining that the detection of the face of the at least one occupant has failed, the processing circuitry matches a center of the newly set search area with a center of the successfully detected face area to expand the search area.

11. The face detection device according to claim 1, wherein the processing circuitry determines that the detection of the face of the at least one occupant has failed when at least a part of the face of the at least one occupant outside a detection area provided in the captured image is detected.

* * * * *